United States Patent
Duchini et al.

(10) Patent No.: US 11,963,853 B2
(45) Date of Patent: Apr. 23, 2024

(54) ROTARY WELDING DEVICE

(71) Applicant: GDM S.p.A., Bologna (IT)

(72) Inventors: Andrea Duchini, Castelleone (IT); Giacomo Noferini, Castenaso (IT); Matteo Piantoni, Albino (IT); Gabriele Resmini, Vailate (IT); Marco Rosani, Vailate (IT); Alessandro Saccomani, Cassano d'Adda (IT); Maurizio Spatti, Sulzano (IT)

(73) Assignee: GDM S.P.A., Bologna (IT)

( * ) Notice: Subject to any disclaimer, the term of this patent is extended or adjusted under 35 U.S.C. 154(b) by 332 days.

(21) Appl. No.: 17/427,858

(22) PCT Filed: Feb. 11, 2020

(86) PCT No.: PCT/IB2020/051066
§ 371 (c)(1),
(2) Date: Aug. 2, 2021

(87) PCT Pub. No.: WO2020/165749
PCT Pub. Date: Aug. 20, 2020

(65) Prior Publication Data
US 2022/0125647 A1   Apr. 28, 2022

(30) Foreign Application Priority Data
Feb. 14, 2019   (IT) .................. 102019000002135

(51) Int. Cl.
*B29C 65/08*   (2006.01)
*A61F 13/15*   (2006.01)
(Continued)

(52) U.S. Cl.
CPC ...... *A61F 13/15739* (2013.01); *B29C 65/087* (2013.01); *B29C 65/7847* (2013.01);
(Continued)

(58) Field of Classification Search
CPC ..... A61F 13/15739; A61F 2013/15869; B29C 65/7847; B29C 66/0062; B29C 66/8322; B29C 66/8412
(Continued)

(56) References Cited

U.S. PATENT DOCUMENTS 5,817,199 A * 10/1998 Brennecke ........ B29C 66/81433
156/580.2
6,368,437 B1   4/2002 Ziegelhoffer et al.
(Continued)

FOREIGN PATENT DOCUMENTS

JP   2005205026 A   8/2005

OTHER PUBLICATIONS

Chinese Office Action dated Mar. 7, 2023 from counterpart Chinese Patent Application No. 202080014279.2.
(Continued)

*Primary Examiner* — James D Sells
(74) *Attorney, Agent, or Firm* — SHUTTLEWORTH & INGERSOLL, PLC; Timothy J. Klima

(57) ABSTRACT

A rotary welding device which includes a rotary part rotating about its axis of rotation, one or more supporting elements for supporting a continuous strip, specifically a strip of nappies, supported by the rotary part, and a plurality of welding units, mounted on the rotary part, for welding the continuous strip; each welding unit is configured to pass from a non-operating position to an operating position and vice versa; each welding unit includes a respective welding tip and a respective anvil element which is movable relative to the welding tip; each welding unit includes respective first movement means configured to drive the anvil element in rotation relative to the welding tip from an initial position, where the anvil element is angularly spaced from the welding tip, to a final position, where the surface of the welding
(Continued)

tip and the surface of the anvil element are parallel and aligned with each other along the same axis, and vice versa.

13 Claims, 7 Drawing Sheets

(51) Int. Cl.
  *B29C 65/00* (2006.01)
  *B29C 65/78* (2006.01)
  *B29L 31/48* (2006.01)
(52) U.S. Cl.
  CPC ...... *B29C 65/7885* (2013.01); *B29C 65/7894* (2013.01); *B29C 66/0062* (2013.01); *B29C 66/1122* (2013.01); *B29C 66/431* (2013.01); *B29C 66/81465* (2013.01); *B29C 66/8226* (2013.01); *B29C 66/8242* (2013.01); *B29C 66/8322* (2013.01); *B29C 66/8324* (2013.01); *B29C 66/83517* (2013.01); *B29C 66/8412* (2013.01); *A61F 2013/15869* (2013.01); *B29C 2793/009* (2013.01); *B29L 2031/4878* (2013.01)

(58) Field of Classification Search
  USPC .......................................................... 156/73.1
  See application file for complete search history.

(56) References Cited

U.S. PATENT DOCUMENTS

| 2004/0106506 | A1 | 6/2004 | Ninomiya et al. |
| 2017/0027763 | A1 | 2/2017 | Fujita et al. |
| 2018/0207877 | A1 | 7/2018 | Sablone et al. |

OTHER PUBLICATIONS

International Search Report and Written Opinion dated May 7, 2020 from counterpart International Patent Application No. PCT/IB2020/051066.

\* cited by examiner

ROTARY WELDING DEVICE

This application is the National Phase of International Application PCT/IB2020/051066 filed Feb. 11, 2020 which designated the U.S.

This application claims priority to Italian Patent Application No, 102019000002135 filed Feb. 14, 2019, which application is incorporated by reference herein.

TECHNICAL FIELD

This invention relates to a rotary welding device.

In particular, the device according to this invention is configured to weld a continuous web along a direction transverse to the web feed direction according to a predetermined weld spacing.

BACKGROUND ART

For example, the device of this invention is configured to weld a continuous strip of absorbent articles, or nappies, to attach the side gathers of nappy pants.

Prior art apparatuses for welding absorbent articles typically comprise a rotary part on whose peripheral surface is placed the continuous strip of absorbent articles to be welded.

A plurality of welding units are configured to weld the continuous strip of nappies while the rotary part rotates through a predetermined circular arc.

The circular arc defines a weld time for the continuous strip, during which each welding unit operates to make the respective weld.

In this context, owing to market demands for high production speeds, the weld time available for each welding unit to perform its welding operation is, at present, just a few seconds.

DISCLOSURE OF THE INVENTION

To ensure that welding is performed correctly by each welding unit in this short space of time, the contact and flatness between the surfaces of the welding element and of the respective anvil, with the continuous strip interposed between them, are therefore of considerable importance.

For this reason, the need was felt to provide a rotary welding device which comprises a rotary part rotating about its axis of rotation, one or more supporting elements for supporting a continuous strip, specifically a strip of absorbent articles, specifically nappies, supported by the rotary part and a plurality of welding unit, mounted on the rotary part, for welding the continuous strip.

Each welding unit is configured to pass from a non-operating position to an operating position and vice versa.

Each welding unit comprises a respective welding tip and a respective anvil element which is movable relative to the welding tip.

Preferably, the welding tip of each welding unit is directed towards the inside of the rotary part and the respective anvil element towards the outside of the rotary part.

Each welding unit comprises respective first movement means configured to drive the anvil element in rotation relative to the welding tip from an initial position, where the anvil element is angularly spaced from the welding tip, to a final position, where the surface of the welding tip and the surface of the anvil element are parallel and aligned with each other along the same axis, and vice versa.

First drive means drive the first movement means to cause the anvil element to pass from the initial position to the final position and vice versa.

The first movement means of each welding unit comprise at least one articulated system comprising a crank, a conrod which is pivotally connected to the crank, and a lever for supporting the anvil element and oscillating about an axis of oscillation.

The oscillation of the lever about the axis of oscillation causes the anvil element to be driven angularly relative to the welding tip from the initial position to the final position, and vice versa.

Advantageously, the final position adopted by the articulated system prevents transmitting the weld forces to the first drive means. In this regard, during the step of welding, the zero or very limited loads transmitted to the first drive means significantly reduce the wear on the drive means and, consequently, the frequency of maintenance required over time.

BRIEF DESCRIPTION OF THE DRAWINGS

Further features of the invention and its advantages are more apparent in the following non-limiting description of preferred but non-exclusive embodiments of a rotary welding device for absorbent articles, as illustrated in the accompanying drawings, in which.

DETAILED DESCRIPTION OF PREFERRED EMBODIMENTS OF THE INVENTION

The numeral 1 in this specification denotes a rotary welding device.

The device 1 of this specification is configured to weld a continuous web 2 according to a weld spacing P.

The continuous web 2 has at least two superposed edges intended to be welded by the device 1 according to a weld spacing P.

The continuous web 2 has a predominant longitudinal extension L.

The device 1 is configured to weld the continuous web 2 along a direction T transverse to the longitudinal direction of extension L.

Figure 1:
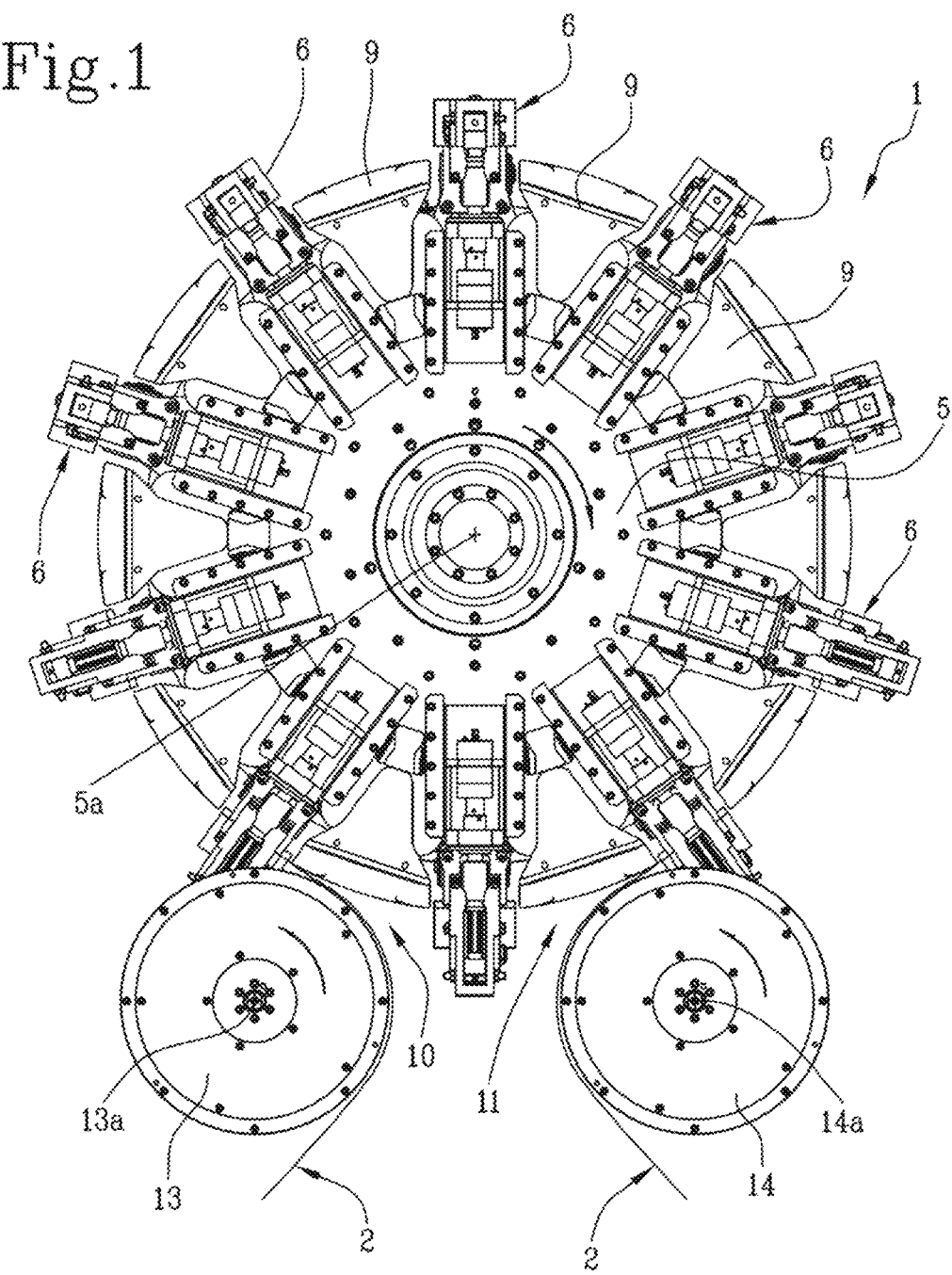
FIG. 1 is a schematic front view of a rotary welding device according to this invention.
Figure 2:
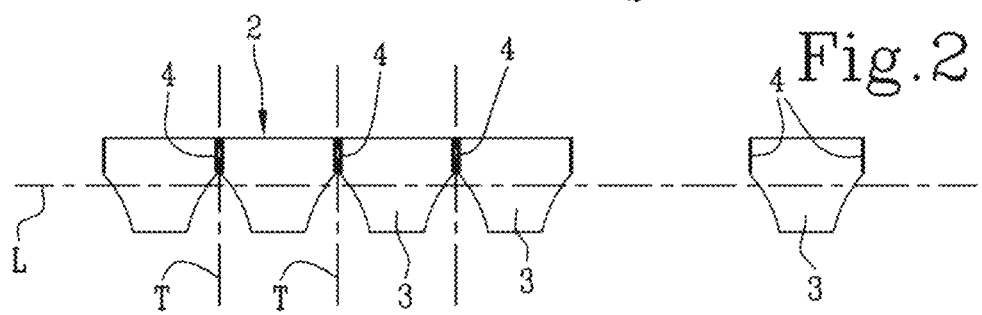
FIG. 2 is a schematic plan view of a continuous strip 2 of absorbent articles welded by the device of FIG. 1.

More specifically, with reference to FIG. 2, the device 1 makes a plurality of welds along the transverse direction T of the continuous web 2 in respective welded zones 4 according to a weld spacing P.

By way of example, the continuous web 2 is a continuous strip of pouches containing liquids, specifically liquid food products such as beverages, for example, or solid food products such as infusion substances.

The device 1 of this specification is configured to weld a continuous strip 2 of absorbent articles, specifically a continuous strip 2 of nappy pants, also known as "baby training pants".

The continuous strip 2 is a succession of absorbent articles 3 folded along the centre line of the absorbent pad.

In this regard, the continuous strip 2 is defined by a continuous succession of superposed elasticized gathers of the respective absorbent articles 3.

The continuous strip 2 has a predominant longitudinal extension L.

The device 1 is configured to weld the continuous strip 2 of absorbent articles along a direction T transverse to the longitudinal direction of extension L.

More specifically, with reference to FIG. 2, the device 1 makes a plurality of welds along the transverse direction T of the continuous strip 2 in respective welded zones 4, each of which is intended to define the transverse weld of superposed elasticized gathers of the respective absorbent articles 3.

The welded zones 4 are necessary to seal the elasticized gather at the waist portion of the absorbent article 3, encircling the wearer's waist.

Downstream of the device 1, cutting means not illustrated separate each absorbent article 3 from the next by cutting the continuous strip 2 at each welded zone 4, in particular at its centre line.

The rotary welding device 1 comprises a rotary part 5 which rotates about its axis of rotation 5a.

The axis of rotation 5a of the rotary part 5 is preferably a horizontal axis.

Alternatively, the axis of rotation 5a of the rotary part 5 is a vertical axis.

The device 1 comprises a plurality of welding units 6 for welding the continuous strip 2.

The welding units 6 are mounted on the rotary part 5 and thus rotate about the axis of rotation 5a of the rotary part 5.

The welding units 6 are equispaced from each other angularly about the axis of rotation 5a of the rotary part 5.

The circumferential spacing at which the welding units 6 are mounted corresponds to the weld spacing of the welded zones 4 of the continuous strip 2 of the absorbent articles 3.

The diameter defined by the spacing of the welding units 6 about the axis of rotation 5a of the rotary part 5 is therefore a changeover parameter.

Each welding unit 6 comprises a respective welding tip 7 and a respective opposing element 8, or anvil element 8, of the welding tip 7.

The anvil element 8 of each welding unit 6 has a contact surface 8a for a respective portion of the continuous strip 2.

The contact surface 8a of the anvil element 8 has an axis 8b which is orthogonal to the surface 8a.

The contact surface 8a has a predetermined welding pattern.

The welding tip 7 of each welding unit 6 has a contact surface 7a for a respective portion of the continuous strip 2.

The contact surface 7a of the welding tip 7 has an axis 7b which is orthogonal to the surface 7a.

Preferably, the welding tip is an ultrasound welding tip 7.

Alternatively, the welding tip 7 is a thermomechanical tip.

Each welding tip 7 of a welding unit 6 is disposed towards the inside of the rotary part 5 and the respective anvil element 8 towards the outside.

Each welding unit is configured to pass from a non-operating position to an operating position and vice versa.

Figure 5:
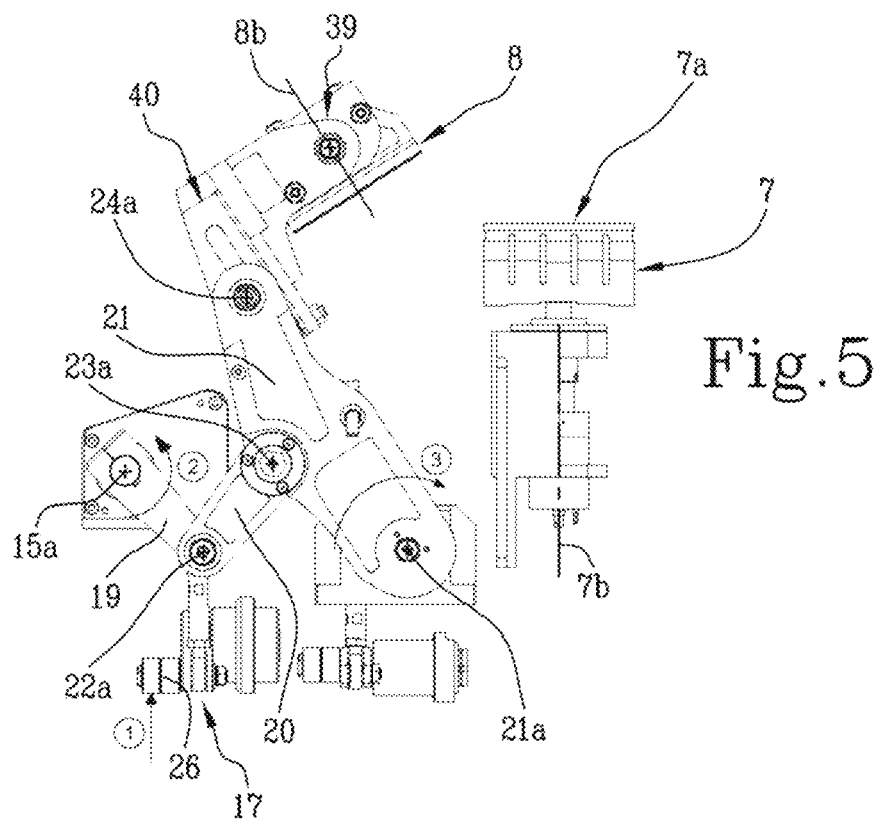
FIG. 5 is a schematic side view of the welding unit of FIG. 4 in a non-operating position.

At the non-operating position, the surface 8a of the anvil element 8 is relatively spaced from the surface 7a of the welding tip 7, which contacts the portion of continuous strip 2 entrained in rotation by the rotary part 5 (see FIG. 5).

At the non-operating position, the axis 7b which is orthogonal to the surface 7a of the welding tip is incident upon the axis 8b which is orthogonal to the surface 8a of the anvil element 8.

Figure 6:
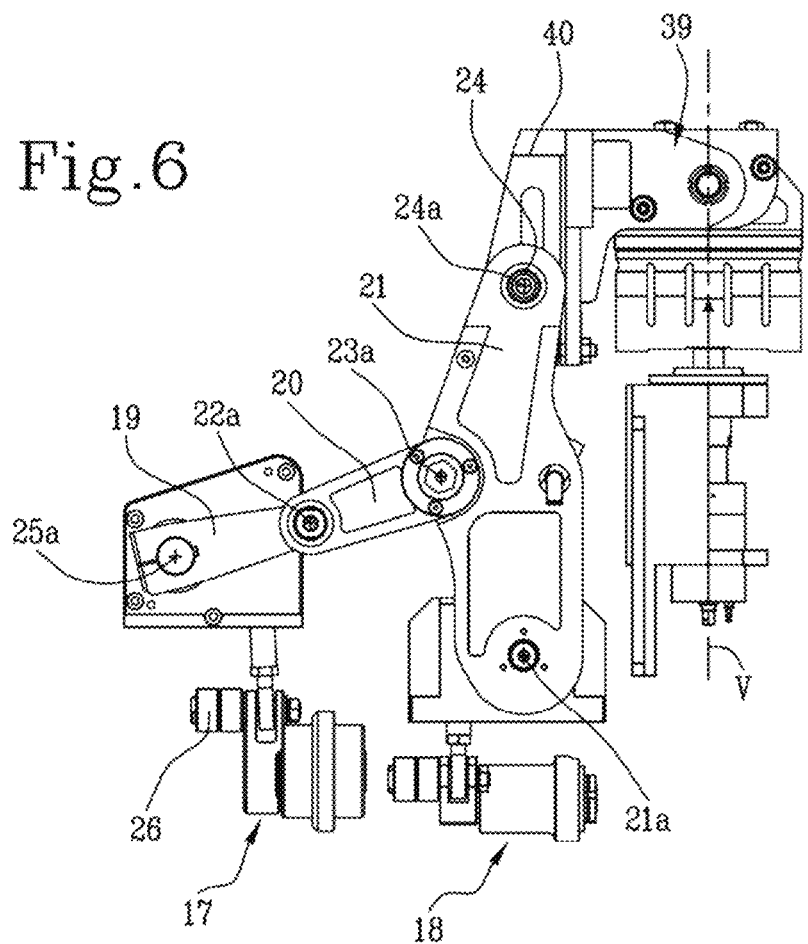
FIG. 6 is a schematic side view of the welding unit of FIG. 4 in an operating position.
Figure 7:
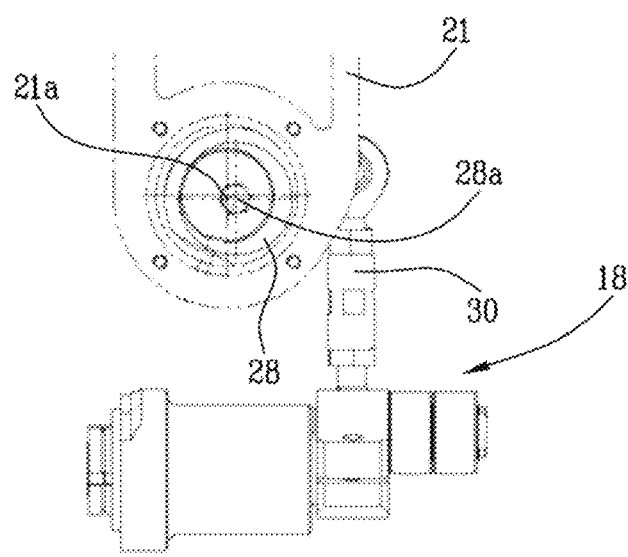
FIG. 7 is a scaled-up view of a detail of the welding unit of FIG. 4.
Figure 8:
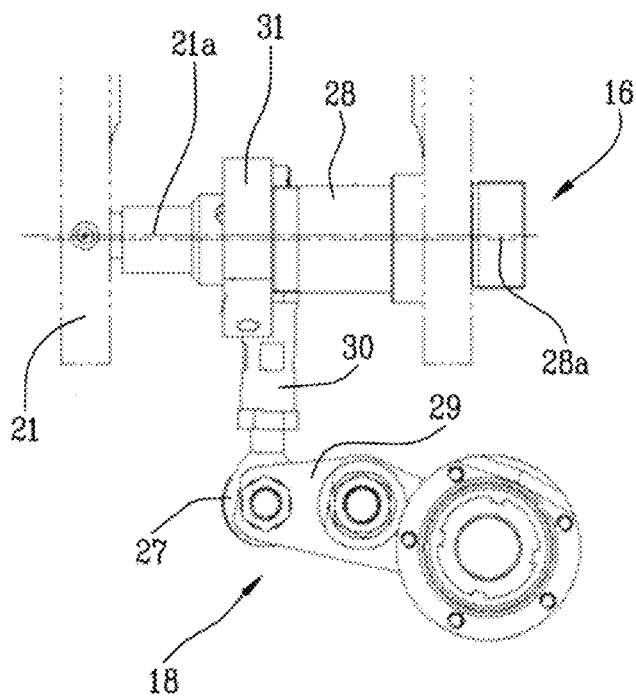
FIG. 8 is a scaled-up view of another detail of the welding unit of FIG. 4.
Figure 9:
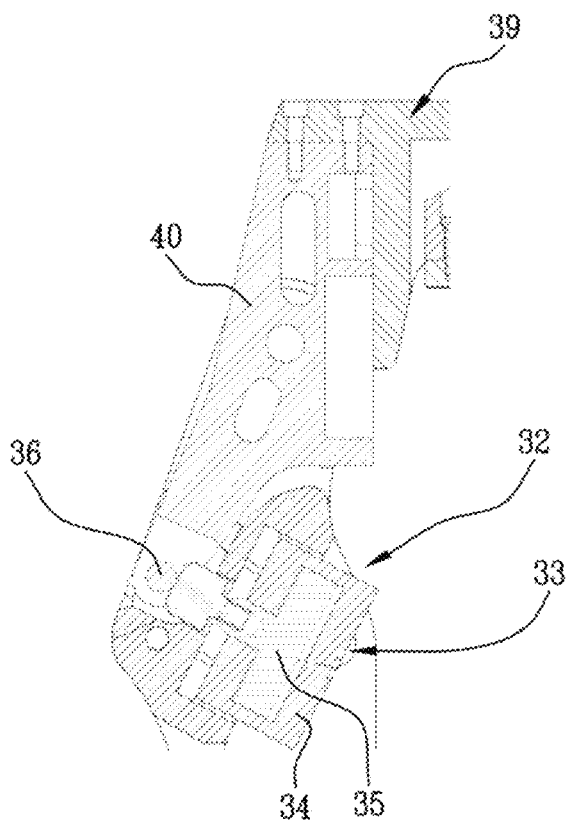
FIG. 9 shows a schematic lateral cross section of the welding unit of FIG. 4.
Figure 10:
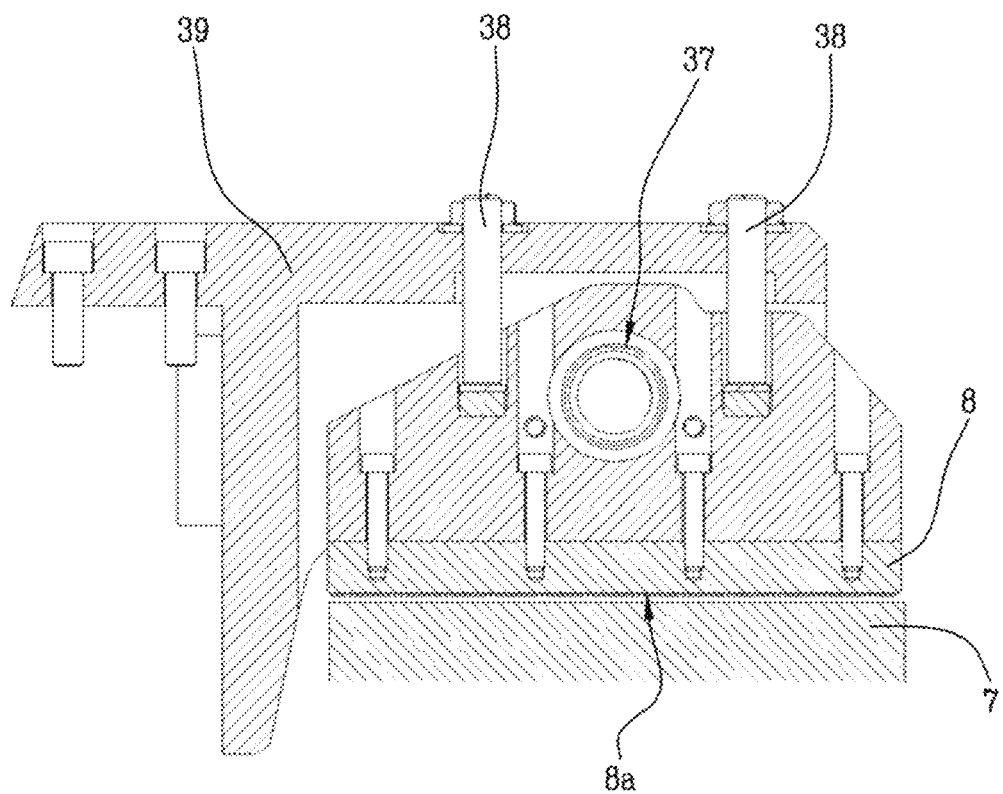
FIG. 10 shows another schematic lateral cross section of the welding unit of FIG. 4.

At the operating position of the welding unit 6, the surface 8a of the anvil element 8 and the surface 7a of the welding tip 7 contact a respective portion of continuous strip 2 interposed between them and intended to become a welded zone 4 (see FIG. 6).

At the operating position, the axis 7b which is orthogonal to the surface 7a of the welding tip and the axis 8b which is orthogonal to the surface 8a of the anvil element 8 are aligned along the same alignment axis V.

The device 1 comprises a plurality of supporting elements 9 for supporting the continuous strip 2.

Figure 3:
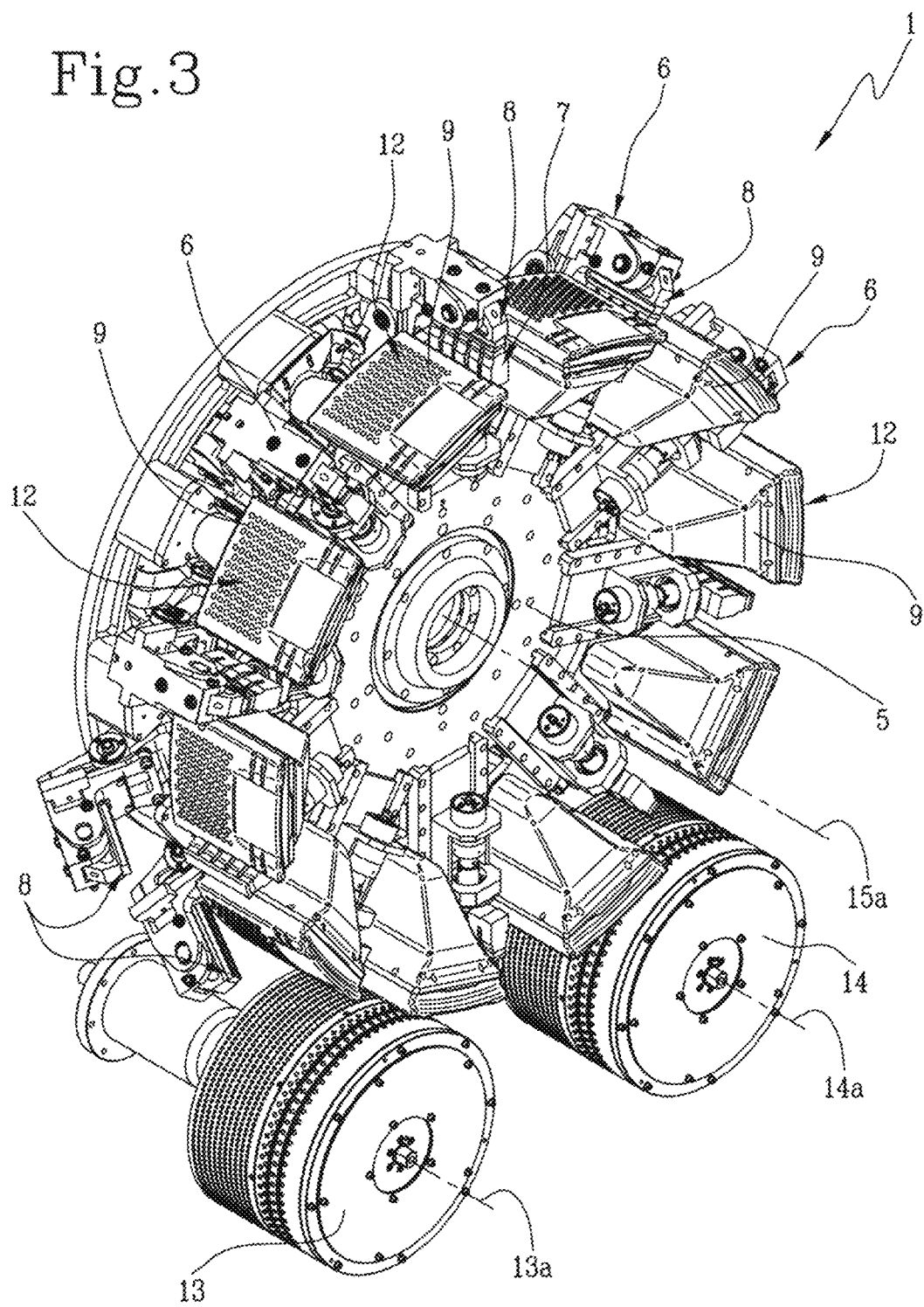
FIG. 3 shows the device of FIG. 1 in a schematic perspective view.
Figure 4:
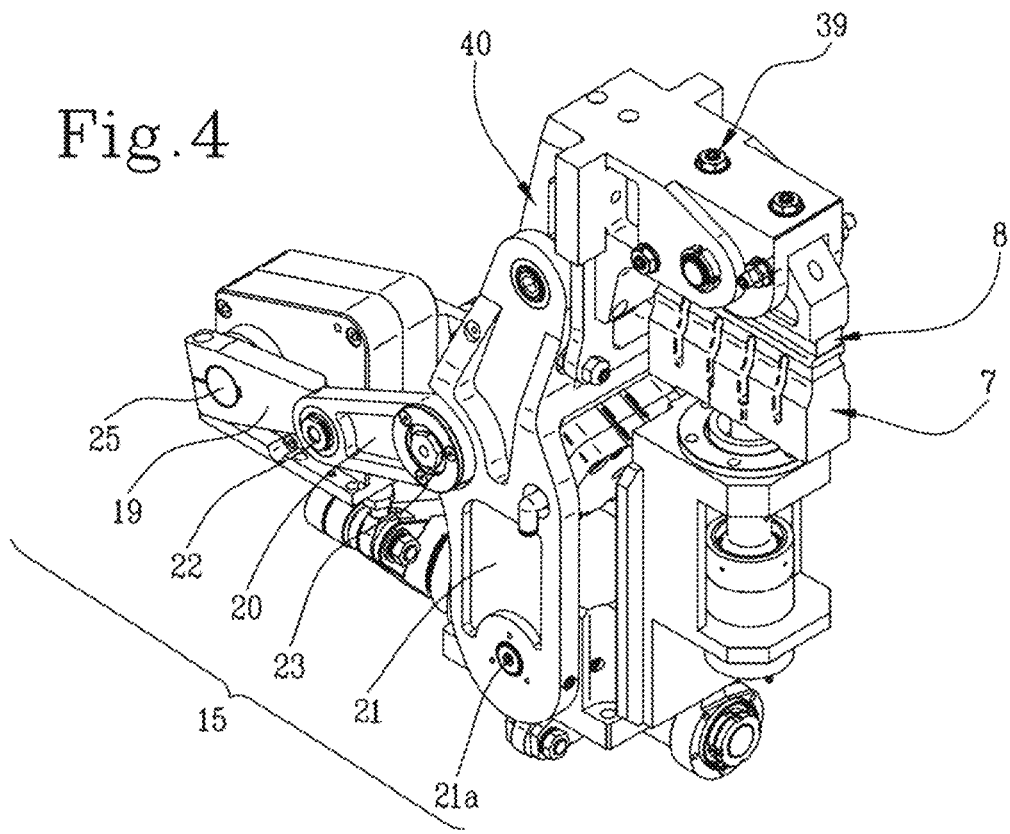
FIG. 4 is a schematic perspective view of the rotary welding device according to this invention.

The supporting elements 9 for supporting the continuous strip 2 are mounted on the rotary part 5 and thus rotate about the axis of rotation 5a of the rotary part 5 (see FIG. 3).

The welding units 6 and the supporting elements 9 are mounted alternately with each other.

In other words, each welding unit 6 is interposed between a respective pair of supporting elements 9.

Each supporting element 9 has a retaining surface 12 for holding the continuous strip 2.

The retaining surface 12 of each supporting element 9 is preferably a curved surface.

Alternatively, the retaining surface 12 of each supporting element 9 is preferably a flat surface.

Preferably, the supporting elements 9 are configured to hold the continuous strip 2 by suction. In this regard, the retaining surface 12 is provided with a pattern of suction holes.

The device 1 comprises a feed station 10 for feeding the continuous strip 2 of the absorbent articles 3 to be welded and an outfeed station 11 for feeding out the welded continuous strip 2.

The continuous strip 2 is fed through the feed station 10 by a roller 13, preferably a suction roller, which rotates about its axis of rotation 13a in such a way that the elasticized gathers of the continuous strip 2 to be welded are wrapped without slipping round the retaining surfaces 12 of the supporting elements 9.

The continuous strip 2 is wrapped round the supporting elements 9 of the device 1 in such a way that the continuous succession of superposed elasticized gathers to be welded faces towards the front of the device accessible to the user.

The welded continuous strip 2 is fed out through the outfeed station 11 by a roller 14, preferably a suction roller, which rotates about its axis of rotation 14a.

The axis of rotation 13a of the feed roller 13 of the continuous strip 2 and the axis of rotation 14a of the conveying roller 14 of the welded continuous strip 2 are parallel. The axis of rotation 5a of the rotary part 5 is parallel to the axes of rotation 13a, 14a of the feed roller 13 of the continuous strip 2 and of the conveying roller 14 of the welded continuous strip 2.

According to this invention, each welding unit 6 comprises first movement means 15 for moving the anvil element 8 relative to the welding tip 7 by imparting a movement whereby the anvil element 8 moves towards the welding tip 7 and a movement whereby the anvil element 8 moves away from the welding tip 7.

The movement towards consists in positioning the anvil element 8 at a position where it is aligned with the welding tip 7—that is to say, a mutual position such that the contact surface 8a of the anvil element 8 is parallel to the contact surface 7a of the welding tip 7 and such that the axis 8b which is orthogonal to the contact surface 8a of the anvil element 8 is aligned with the axis 7b which is orthogonal to the contact surface 7a of the welding tip 7 along the same alignment axis V.

The first movement means 15 are configured to drive the anvil element 8 in rotation relative to the welding tip 7 from an initial position, where the anvil element 8 is angularly spaced from the welding tip 7, to a final position, where the surface 7a of the welding tip 7 and the surface 8a of the anvil element 8 are parallel and aligned with each other along the same alignment axis V, and vice versa.

At the initial position, the direction of the axis 8b which is orthogonal to the surface 8a of the anvil element 8 is incident upon the direction of the axis 7b which is orthogonal to the surface 7a of the welding tip 7, in particular in such a way as to make an acute angle.

The first movement means 15 comprise at least one articulated system comprising a crank 19, a conrod 20 which is pivotally connected to the crank 19, and a lever 21 for supporting the anvil element 8.

The crank 19, the conrod 20 and the lever 21 define an articulated "toggle" system.

In other words, the crank 19 of the first movement means 15 defines a first element configured to rotate about an axis of rotation.

The conrod 20 of the first movement means 15 defines a second element, pivotally connected to the first element 19, configured to perform a translational movement along a feed direction.

The lever 21 of the first movement means 15 defines a third element configured to oscillate about an axis of oscillation.

With reference to each welding unit 6, the first movement means 15 comprise a double articulated "toggle" system, positioned to face each other and driven synchronously.

More specifically, the cranks 19 of the articulated systems of each welding unit 6 are driven in rotation by the rotation of the same shaft 25, which rotates about its axis of rotation 25a.

The cranks 19 of the articulated systems of each welding unit 6 are connected to the shaft 25 at respective ends of the shaft 25, opposite each other.

More specifically, a connecting clamp connects the cranks 19 of the articulated systems of each welding unit 6 to respective ends of the shaft 25.

Each conrod 20 is connected to a respective crank 19 by a pin 22.

Each conrod 20 is pivotally connected to the pin 22 of the crank 19.

The pin 22 for connecting the conrod 20 to the respective crank 19 is integral with the crank 19 and rotates about the axis of rotation 25a of the shaft 25.

The conrods 20 of the double articulated "toggle" system are connected to a single lever 21, preferably at respective centre line portions of the lever 21.

Each conrod 20 is connected to a respective portion of the lever 21 by a pin 23 which is integral with the lever 21.

Each conrod 20 is pivotally connected to the pin 23 of the respective portion of the lever 21.

Each conrod 20 is pivotally connected to a respective crank 19 and to a respective portion of the lever 21 at respective ends, preferably opposite each other.

More specifically, the end of the conrod 20 connected to the crank 19 rotates about a respective axis 22a.

More specifically, the end of the conrod 20 connected to the lever 21 rotates about a respective axis 23a.

The lever 21 oscillates about its axis of oscillation 21a.

The oscillation of the lever 21 about the axis of oscillation 21a causes the anvil element 8 to move towards and away from the welding tip 7—that is to say, causes the anvil element 8 to pass from the initial position to the final position, and vice versa, relative to the welding tip 7.

On the opposite side with respect to the axis of oscillation 21a of the lever 21, the lever 21 is configured to support a supporting member 39 of the anvil element 8.

More precisely, a supporting element 40 of the supporting member 39 is pivotally connected to the lever 21.

In particular, the supporting element 40 is pivotally connected to each lever 21 by a respective pin 24, which rotates about its axis 24a.

The pins 24 are integral with the supporting element 40.

Thus, with reference to the movement of the anvil element 8 towards the welding tip 7, when the first movement means 15 pass from the initial position to the final position, the crank 19 of each articulated system is driven in rotation by the shaft 25 about the axis of rotation 25a, specifically clockwise with reference to FIG. 5.

The rotation of the crank 19 causes the respective conrod 20 to move, which in turn drives the respective lever 21 to oscillate about the axis of oscillation 21a, clockwise with reference to FIG. 5, so that the anvil element 8 passes from the initial position to the final position, and vice versa, relative to the welding tip 7.

The final position is reached when the contact surface 8a of the anvil element 8 is parallel to the contact surface 7a of the welding tip 7 and the two are aligned along the same alignment axis V.

At the final position of the anvil element 8 relative to the welding tip 7, the lever 21, in the preferred embodiment, is disposed along a line parallel to the alignment axis V.

At the final position of the anvil element 8 relative to the welding tip 7, the crank 19 and the conrod 20 are aligned with each other at a position inclined to the position of the lever 21.

A counter-rotation of the crank 19, clockwise with reference to the embodiment illustrated, causes the respective conrod 20 to move, which in turn drives the respective lever 21 to oscillate about the axis of oscillation 21a, anticlockwise with reference to the embodiment illustrated, so that the anvil element 8 moves away from the welding tip 7—that is to say, passes from the final position to the initial position.

First drive means 17 drive the common shaft 25 in rotation about its axis 25a.

Preferably, the first drive means 17 are cam drive means.

The first drive means 17 comprise a cam, not illustrated, and a follower 26, driven by the cam.

Each welding unit 6 comprises a respective follower 26 of the first drive means 17.

The follower 26 is configured to translate to a raised position relative to a rest position to cause the shaft 25 to rotate about its axis 25a, which in turn causes the anvil element 8 to move towards the welding tip 7—that is to say, to pass from the initial position to the final position.

The translation of the follower 26 from the raised position to the rest position causes the shaft 25 to rotate about its axis 25*a*, in the direction opposite to that which imparted the rotation by which the follower was translated from the rest position to the raised position, which in turn causes the anvil element 8 to move away from the welding tip 7—that is to say, to pass from the final position to the initial position.

The configuration adopted by the crank 19, conrod 20 and lever 21 at the final position of the anvil element 8 relative to the welding tip 7, is such that the welding forces are not transferred to the first drive means 17, since the forces are demultiplied by the configuration adopted by the crank 19, conrod 20 and lever 21.

Each welding unit 6 comprises second movement means 16 for moving the anvil element 8 relative to the welding tip 7 from a starting position, where the contact surface 8*a* of the of the anvil element 8 and the contact surface 7*a* of the welding tip 7 are parallel and aligned with each other along the same alignment axis V, to an arrival position, where the contact surface 8*a* of the anvil element 8 and the contact surface 7*a* of the welding tip 7 contact the continuous strip 2 interposed between them.

The arrival position corresponds to the operating position of the welding unit 6.

From the starting position to the arrival position, the anvil element 8 translates towards the respective welding tip 7 until it comes into contact with the continuous strip 2 that is interposed between them.

Conversely, the second movement means 16 are configured to translate the anvil element 8 away from the welding tip 7, thus disengaging the continuous strip 2 interposed between them.

The second movement means 16 are driven by second drive means 18.

The second movement means 16 comprise a shaft 28 which rotates about its axis of rotation 28*a*.

The lever 21 of the first movement means 15 is connected to the shaft 28 of the second movement means 16 at the end of it that oscillates about its axis 21*a*.

The second drive means 18 comprise a cam, not illustrated, and a follower 27, driven by the cam.

Each welding unit 6 comprises a respective follower 27 of the second drive means 18.

The second drive means 18 comprise a lever 29, connected to the follower 27.

The second drive means 18 comprise a conrod 30, connected to the lever 29, which is in turn connected to the shaft 28 by an element 31 that rotates about the axis of rotation 28*a* of the shaft 28.

The element 31 connecting the conrod 30 to the shaft 28 is in the form of a clamp.

The axis of rotation 21*a* of the shaft 28 connected to the lever 21 that supports the anvil element 8 is eccentric relative to the axis of rotation 28*a* of the shaft 28 to which the element 31 connected to the conrod 30 of the second drive means 18 is connected.

In use, the lifting of the follower 27, by operation of the cam, allows setting in rotation the shaft 28 to which the lever 21 that supports the anvil element 8 is connected.

The eccentricity between the axis of rotation 28*a* of the shaft 28 and the axis of oscillation 21*a* of the lever 21 allows translating the lever 21 that supports the anvil element 8 in such a way as to move the anvil element 8 closer to the welding tip 7 until contact is made with a zone of the continuous strip 2 interposed between the surface 8*a* of the anvil element 8 and the surface 7*a* of the welding tip 7.

Conversely, the lowering of the follower 27 causes the shaft 28 to which the lever 21 is connected to rotate in the direction opposite to that imparted in order to lift the follower 27, thus causing the lever 21 that supports the anvil element 8 to be translated in such a way as to move the anvil element 8 away from the welding tip 7, thereby disengaging the welded zone of the continuous strip 2.

Each welding unit 6 comprises a pneumatic system 32 for keeping the surface 8*a* of the anvil element 8 against the surface 7*a* of the welding tip 7, with the zone of the continuous strip 2 to be welded interposed between them.

The pneumatic system 32 allows applying and maintaining a predetermined pressure between the anvil element 8 and the welding tip 7 so that the pressure remains as constant as possible during the entire welding process—that is, for as long as the welding unit 6 is at the operating position.

The zone of the continuous strip 2 that is interposed between the surface 8*a* of the anvil element 8 and the surface 7*a* of the welding tip 7 is welded when the welding tip 7 is actuated to make the welded zone 4.

The pneumatic system 32 comprises an actuator 33 configured to remain active at all times.

The actuator 33 comprises a cylinder 34 and a piston 35 which is slidably disposed inside the cylinder 34.

The cylinder 34 is connected to the lever 21 that supports the anvil element 8.

The piston 35 butts against an abutment element 36.

The abutment element 36 of the piston 35 is disposed in the supporting element 40.

The action applied by the piston 35 on the abutment element 36 causes the supporting element 40 to rotate relative to the lever 21 about the axis 24*a* of the pin 24, allowing the force generated by the actuator 33 against the welding tip 7, in the operating configuration of the welding unit 6, or the force generated by the actuator 33 against locking means not illustrated, in the operating configuration of the welding unit 6, to be discharged.

In effect, since the actuator 33 of the pneumatic system 32 is active at all times, in the operating configuration of the welding unit 6, the force generated by the actuator 33 is discharged against locking means not illustrated.

Once the process of welding the zone of the continuous strip 2 is over, the welding unit 6 passes from the operating position to the non-operating position as the first and second movement means 15, 16 move the anvil element 8 away from the welding tip 7.

More specifically, the second movement means 16 drive the lever 21 that supports the anvil element 8 to be translated in such a way as to move the anvil element 8 away from the welding tip 7—that is, to pass from the arrival position to the starting position—and the first movement means 15 drive the anvil element 8 to rotate in such a way as to move away from the welding tip 7—that is, to pass from the final position to the initial position.

Generally speaking, the overall movement of the anvil element 8 towards the welding tip 7 is the result of the combination of the first and second movements driven, respectively, by the first and second drive means 17 and 18, which may operate in parallel or in series.

It should be noted that the working arc in which the continuous strip 2 is welded, where each welding unit 6 is at the operating position, is located in the zone of the circle of the rotary part 5 diametrically opposite the zone where the feed roller 13 for feeding the continuous strip 2 and the conveying roller 14 for feeding out the continuous strip are located.

The movement imparted by the first and second movement means 15, 16 to move the anvil element 8 of each welding unit 6 from the initial position to the final position, and vice versa, must be extensive enough to prevent collisions between the mechanical elements disposed within the arc of the rotary part 5 included between the feed station 10 and the outfeed station 11.

Once the action of the welding tip 7 has been completed, the second drive means 16 drive the anvil element 8 be translated away from the welding tip 7 and the first movement means 15 drive the anvil element 8 to move away from the welding tip 7.

Advantageously, the first and second drive means 15, 16 according to this specification allow isolating the mechanical drives from the loads associated with the welding process.

More specifically, thanks to the geometrical "toggle" configuration of the first movement means 15, the welding forces are not transferred, or are transferred only minimally, to the first drive means 17 and to the second drive means 18.

In this regard, the zero or very limited loads transmitted to the first drive means 17 and to the second drive means 18 during the step of welding significantly reduce the wear on the devices and, consequently, the frequency of maintenance required over time.

The geometrical "toggle" configuration of the first movement means 15 also allows ensuring that the forward movements and final positioning of the anvil element 8 are very precise, thus making for a more reliable welding process.

In order to ensure that the surface of the anvil element 8 and the surface of the welding tip 7 are coplanar with each other, a ball joint 37 allows the surface 8a of the anvil element 8 to move relative to the supporting member 39 that supports the anvil element 8.

The relative movement of the anvil element 8 allows disposing the surface 8a of the anvil element 8 so it is parallel to the surface 7a of the welding tip 7 so that the welding force required for correctly welding the continuous strip 2 can be provided.

The supporting member 39 comprises limit stop elements 38 which limit the possible rotations of the anvil element 8 while the continuous strip 2 is being welded.

Use of the ball joint has the advantage of allowing independent correction of imprecise alignment of welding parts due to tolerances inherent in component assembly and system settings.

The mechanical limit stop elements prevent excessive movements away from the working position, thus limiting the oscillations which the anvil element 8 can perform while it is being moved.

Figure 11:
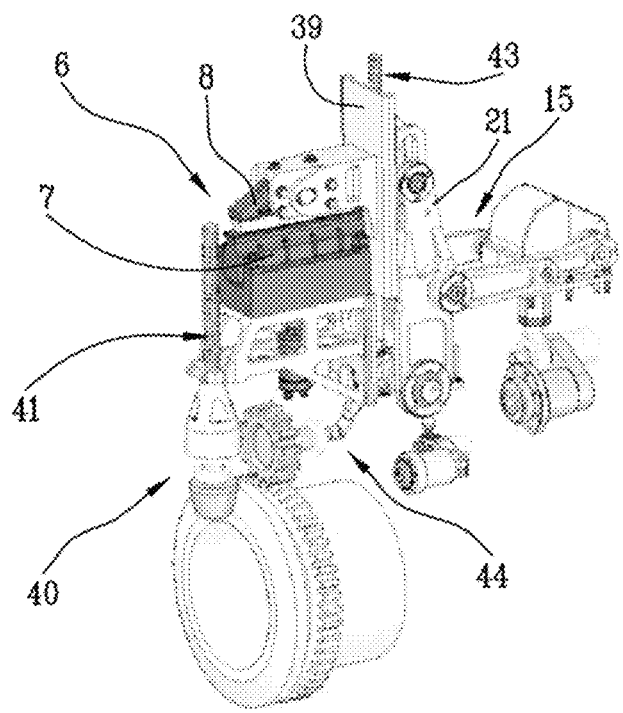
FIGS. 11 and 12 are schematic perspective views of the rotary welding device according to this invention in a first and a second configuration as a function of the weld spacing.
Figure 12:
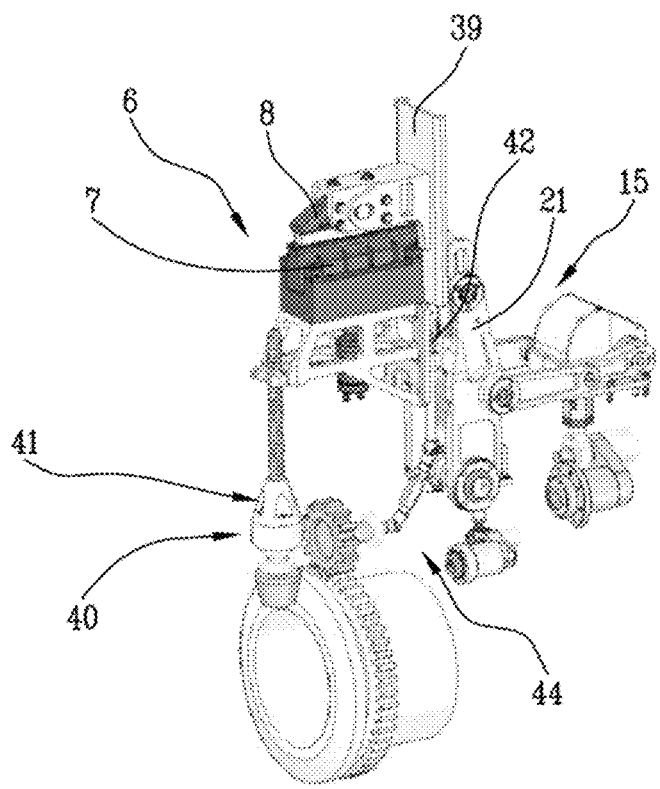

As may be observed in FIGS. 11 and 12, each welding unit 6 comprises third movement means 40 for moving at least the welding tip 7 and the respective anvil element 8 and configured to move the welding tip 7 and the respective anvil element 8 towards or away from the axis of rotation 5a of the rotary part 5 so as to vary the radial position of each welding unit 6 relative to the axis of rotation 5a of the rotary part 5.

The third movement means 40 comprise a first movement member 41 for moving the welding tip 7 and a second movement member 42 for moving the anvil element 8.

The first movement member 41 and the second movement member 42 are driven by the same actuating member 43.

The first movement member 41 and the second movement member 42 are, for example, in the form of rods, each rotating about a respective axis of rotation and having a helical profile along its external peripheral surface.

Thanks to a lead nut and screw coupling, the rotation of the rod of the first movement member 41 and of the second movement member 42 is converted into translational motion for moving the welding tip 7 or the anvil element 8 in parallel with the axis of rotation of the rod.

The second movement member 42 for moving the anvil element 8, which is connected to the lever 21 of the articulated system, is configured to move the supporting member 39 of the anvil element 8 relative to the lever 21 itself.

More specifically, the rod of the second movement member 42 is connected to the lever 21.

The third movement means 40 comprise motion transmission means 44, which are interposed between the actuating member 43 and the second movement member 42 for moving the anvil element 8, and which are configured to move the anvil element 8 relative to the lever 21 when the lever 21 is disposed along a line parallel to the alignment axis V or along a line inclined to the alignment axis V.

More specifically, the transmission means 44 comprise a cardan joint.

This invention also relates to a rotary welding method comprising a step of conveying a continuous strip 2, specifically a strip of absorbent articles 3, at least along a circular arc.

The step of conveying is carried out by the rotary part 5 rotating about its axis of rotation 5a.

The method comprises a step of welding the continuous strip 2 during the step of conveying the continuous strip 2.

The step of welding is carried out by the welding unit 6, which comprises a respective welding tip 7 and a respective anvil element 8.

The step of welding comprises a first sub-step of rotating an anvil element 8 relative to a welding tip 7, or vice versa, to pass from an initial position, where the anvil element 8 is angularly spaced from the welding tip 7, to a final position, where the surface 7a of the welding tip 7 and the surface 8a of the anvil element 8 are parallel and aligned with each other along the same alignment axis V, and vice versa.

The step of welding comprises, after the first sub-step, a second sub-step of translating the anvil element 8 relative to a welding tip 7, or vice versa, from a starting position, where the surface 7a of the welding tip 7 and the surface 8a of the anvil element 8 are parallel and aligned with each other along the same alignment axis V, to an arrival position, where the contact surface 8a of the anvil element 8 and the contact surface 7a of the welding tip 7 contact a respective portion of continuous strip 2 in a respective zone interposed therebetween, and vice versa.

The method comprises a step of varying the position of the anvil element 8 and of the welding tip 7 relative to a fixed reference as a function of the weld spacing of the continuous strip 2. The fixed reference is the axis of rotation 5a of the rotary part 5.

The invention claimed is:

1. A rotary welding device comprising:
   a rotary part rotating about a first axis of rotation,
   one or more supporting elements for supporting a continuous strip of absorbent articles, supported by the rotary part,
   a plurality of welding units, mounted on the rotary part, for welding the continuous strip;
   each welding unit being configured to pass from a non-operating position to an operating position and vice versa;

each welding unit comprising a respective welding tip and a respective anvil element which is movable relative to the welding tip;

the welding tip of each welding unit being directed towards an inside of the rotary part and the respective anvil element towards an outside of the rotary part;

each welding unit comprising a respective first movement mechanism configured to drive the anvil element in rotation relative to the welding tip from an initial position, where the anvil element is angularly spaced from the welding tip, to a final position, where a contact surface of the welding tip and a contact surface of the anvil element are parallel and aligned with each other along a second axis, and vice versa;

a respective first drive mechanism configured to drive the first movement device to cause the anvil element to pass from the initial position to the final position and vice versa;

the first movement mechanism of each welding unit comprising at least one articulated system comprising a crank, a conrod, connected to the crank, and a lever, connected to the conrod, for supporting the anvil element and oscillating about an axis of oscillation; the oscillating of the lever causing the anvil element to be driven angularly relative to the welding tip from the initial position to the final position, and vice versa.

2. The device according to claim 1, wherein the at least one articulated system comprising a pair of the articulated systems which confront each other and whose cranks are linked to a same rotation shaft; the conrod of each articulated system being connected to a respective crank and being connected to a single lever; the first drive mechanism being configured to rotationally drive the shaft which the cranks of the first movement mechanism are connected to.

3. The device according to claim 1, wherein each welding unit comprises a second movement mechanism configured for moving the anvil element relative to the welding tip from a starting position, where the contact surface of the welding tip and the contact surface of the anvil element are parallel and aligned with each other along the second axis, to an arrival position, where the contact surface of the anvil element and the contact surface of the welding tip contact a respective portion of the continuous strip in a respective zone interposed therebetween, and vice versa.

4. The device according to claim 3, wherein the second movement mechanism comprises a shaft which rotates about a third axis of rotation and which is connected to the lever of the first movement mechanism; an eccentricity between the third axis of rotation of the shaft and the axis of oscillation of the lever that supports the anvil element causes a translational movement of the anvil element towards or away from the welding tip, and vice versa.

5. The device according to claim 4, and further comprising a second drive mechanism that rotationally drives the shaft which the lever of the first movement mechanism is connected to.

6. The device according to claim 1, wherein each welding unit comprises a pneumatic system for keeping the contact surface of the anvil element against the zone of the continuous strip that is interposed between the contact surface of the anvil element and the contact surface of the welding tip.

7. The device according to claim 6, wherein the pneumatic system comprises a cylinder and a piston which is slidably disposed inside the cylinder; the cylinder being connected to the lever that supports the anvil element and the piston being configured to operate against an abutment element located in a supporting element for supporting the anvil element; the supporting element being pivotally connected to the lever of the first movement mechanism.

8. The device according to claim 1, and further comprising a supporting member, supported by the lever of the anvil element which comprises a ball joint configured to allow the anvil element to rotate relative to the supporting member.

9. The device according to claim 8, wherein the supporting member comprises limit stop elements which limit possible rotations of the anvil element.

10. The device according to claim 1, wherein each welding unit comprises a third movement mechanism for moving at least the welding tip and the respective anvil element and configured to move the welding tip and the respective anvil element towards or away from the first axis of rotation to vary a radial position of the welding tip and of the respective anvil element relative to the first axis of rotation.

11. The device according to claim 10, wherein the third movement mechanism comprises a first movement member for moving the welding tip and a second movement member for moving the anvil element; the first movement member and the second movement member being driven by a same actuating member.

12. The device according to claim 11, wherein the second movement member for moving the anvil element, which is connected to the lever of the at least one articulated system, is configured to move the supporting member of the anvil element relative to the lever.

13. The device according to claim 12, wherein the third movement mechanism comprises a motion transmission mechanism which is interposed between the actuating member and the second movement member for moving the anvil element, and which is configured to move the anvil element relative to the lever when the lever is disposed along a line parallel to the second axis or along a line inclined to the second axis.

* * * * *